(12) United States Patent
Miyaki et al.

(10) Patent No.: US 8,034,736 B2
(45) Date of Patent: Oct. 11, 2011

(54) CATALYST FOR SYNTHESIZING ACRYLONITRILE AND PROCESS FOR PRODUCING ACRYLONITRILE

(75) Inventors: Kenichi Miyaki, Yokohama (JP); Motoo Yanagita, Yokohama (JP); Hirokazu Watanabe, Yokohama (JP); Takashi Karasuda, Yokohama (JP)

(73) Assignee: Dia-Nitrix Co., Ltd., Tokyo (JP)

( * ) Notice: Subject to any disclaimer, the term of this patent is extended or adjusted under 35 U.S.C. 154(b) by 274 days.

(21) Appl. No.: 12/398,619

(22) Filed: Mar. 5, 2009

(65) Prior Publication Data

US 2009/0234149 A1    Sep. 17, 2009

(30) Foreign Application Priority Data

Mar. 14, 2008  (JP) ................................ 2008-066697

(51) Int. Cl.
*B01J 21/02* (2006.01)
*C07C 253/18* (2006.01)

(52) U.S. Cl. ........................................ 502/205; 502/206

(58) Field of Classification Search .................. 502/205; 558/322

See application file for complete search history.

(56) References Cited

U.S. PATENT DOCUMENTS

| | | | |
|---|---|---|---|
| 3,668,147 A | 6/1972 | Yoshino et al. | |
| 3,988,359 A | 10/1976 | Saito et al. | |
| 4,049,575 A | 9/1977 | Sasaki et al. | |
| 4,083,804 A | 4/1978 | Saito et al. | |
| 4,370,279 A | 1/1983 | Sasaki et al. | |
| 4,536,483 A | 8/1985 | Sasaki et al. | |
| 5,132,269 A | 7/1992 | Sasaki et al. | |
| 5,840,648 A | 11/1998 | Suresh et al. | |
| 6,653,496 B1 | 11/2003 | Mori et al. | |

FOREIGN PATENT DOCUMENTS

| | | |
|---|---|---|
| EP | 0 083 189 | 7/1983 |
| EP | 0 323 129 A1 | 7/1989 |
| JP | 38-17967 | 9/1963 |
| JP | 38-19111 | 9/1963 |
| JP | 46-2804 | 1/1971 |
| JP | 47-18722 | 5/1972 |
| JP | 47-18723 | 5/1972 |
| JP | 47-19765 | 6/1972 |
| JP | 47-19766 | 6/1972 |
| JP | 47-19767 | 6/1972 |
| JP | 50-108219 | 8/1975 |
| JP | 52-125124 | 10/1977 |
| JP | 59-139938 | 8/1984 |
| JP | 59-204163 | 11/1984 |
| JP | 61-13701 | 4/1986 |
| JP | 1-228950 | 9/1989 |
| JP | 4-118051 | 4/1992 |
| JP | 7-47272 | 2/1995 |
| JP | 10-43595 | 2/1998 |
| JP | 11-169715 | 6/1999 |
| JP | 2001-114740 | 4/2001 |

OTHER PUBLICATIONS

U.S. Appl. No. 12/446,759, filed Apr. 23, 2009, Yanagita et al.

*Primary Examiner* — Kamal Saeed
(74) *Attorney, Agent, or Firm* — Oblon, Spivak, McClelland, Maier & Neustadt, L.L.P.

(57) ABSTRACT

A catalyst for synthesizing acrylonitrile that enables acrylonitrile to be synthesized at high yield, and a process for producing acrylonitrile using that catalyst, are provided. A catalyst for synthesizing acrylonitrile is used having a composition represented by $Fe_a Sb_b C_c D_d Te_e F_f X_x Y_y Z_z O_g (SiO_2)_h$. In the formula, component C represents at least one element selected from the group consisting of Cu, Ni and Co, component D from the group consisting of Mo, W and V, component F from the group consisting of P and B, component X from the group consisting of Sn, Ti, Zr, Nb, Ta, Cr, Ru, Pd, Ag, Al, Ga, In, Tl, Ge, As, Bi, La, Ce, Pr, Nd and Sm, component Y from the group consisting of Mg, Ca, Sr, Ba, Mn, Zn and Pb, and component Z from the group consisting of Li, Na, K, Rb and Cs, and $SiO_2$ represents silica, when a=10, b=5 to 60, c=0.1 to 8.0, d=0.1 to 4.0, e=0.1 to 5.0, f=1.3 to 5.0, x=0 to 5, y=0 to 5, z=0 to 2, h=10 to 200 and g is the atomic ratio of oxygen required to satisfy the valence of each of the elements excluding silicon, and f/d=1 to 5.

3 Claims, No Drawings

CATALYST FOR SYNTHESIZING ACRYLONITRILE AND PROCESS FOR PRODUCING ACRYLONITRILE

TECHNICAL FIELD

The present invention relates to a catalyst for synthesizing acrylonitrile by vapor phase ammoxidation of propylene by molecular oxygen and ammonia, and to a process for producing acrylonitrile using that catalyst.

The present application claims priority based on Japanese Patent Application No. 2008-066697, filed in Japan on Mar. 14, 2008, the content of which is incorporated herein by reference.

BACKGROUND ART

Methods for vapor phase ammoxidation of propylene by molecular oxygen and ammonia in the presence of a catalyst are widely known as methods for producing acrylonitrile. Various catalysts have been proposed thus far for use as catalysts used at that time.

For example, Patent Document 1 discloses a complex oxide catalyst of antimony, iron and at least one element selected from the group consisting of cobalt and nickel.

In addition, Patent Documents 2 to 8 disclose complex oxide catalysts containing, for example, iron, antimony and tellurium as well as vanadium, molybdenum and tungsten. Moreover, Patent Documents 9 to 11 disclose processes for preparing these catalysts containing iron and antimony.

In addition, Patent Documents 12 to 19 disclose complex oxide catalysts containing molybdenum, bismuth, iron and the like.

[Patent Document 1] Japanese Examined Patent Application, Second Publication No. S38-19111
[Patent Document 2] Japanese Examined Patent Application, Second Publication No. S46-2804
[Patent Document 3] Japanese Examined Patent Application, Second Publication No. S47-19765
[Patent Document 4] Japanese Examined Patent Application, Second Publication No. S47-19766
[Patent Document 5] Japanese Examined Patent Application, Second Publication No. S47-19767
[Patent Document 6] Japanese Unexamined Patent Application, First Publication No. S50-108219
[Patent Document 7] Japanese Unexamined Patent Application, First Publication No. S52-125124
[Patent Document 8] Japanese Unexamined Patent Application, First Publication No. H4-118051
[Patent Document 9] Japanese Examined Patent Application, Second Publication No. S47-18722
[Patent Document 10] Japanese Examined Patent Application, Second Publication No. S47-18723
[Patent Document 11] Japanese Unexamined Patent Application, First Publication No. S59-139938
[Patent Document 12] Japanese Examined Patent Application, Second Publication No. S38-17967
[Patent Document 13] Japanese Unexamined Patent Application, First Publication S59-204163
[Patent Document 14] Japanese Examined Patent Application, Second Publication No. S61-13701
[Patent Document 15] Japanese Unexamined Patent Application, First Publication H1-228950
[Patent Document 16] Japanese Unexamined Patent Application, First Publication H7-47272
[Patent Document 17] Japanese Unexamined Patent Application, First Publication H10-43595
[Patent Document 18] Japanese Unexamined Patent Application, First Publication H11-169715
[Patent Document 19] Japanese Laid-Open Patent Application No. 2001-114740

DISCLOSURE OF THE INVENTION

Problems to be Solved by the Invention

However, these catalysts were not necessarily satisfactory in terms of the yield of acrylonitrile, thus resulting in a need to further improve these catalysts from an industrial viewpoint.

An object of the present invention is to provide a catalyst for synthesizing acrylonitrile capable of synthesizing acrylonitrile at high yield, and to provide a process for producing acrylonitrile.

Means for Solving the Problems

As a result of conducting extensive studies on a catalyst for synthesizing acrylonitrile containing iron, antimony and tellurium, the inventors of the present invention found that by further compounding these components with specific components at specific ratios, a catalyst demonstrating a high acrylonitrile yield can be obtained, thereby leading to completion of the present invention.

Namely, the catalyst for synthesizing acrylonitrile of the present invention is characterized by having the composition represented by the following general formula:

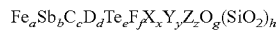

$$Fe_aSb_bC_cD_dTe_eF_fX_xY_yZ_zO_g(SiO_2)_h$$

In the formula, Fe represents iron, Sb represents antimony, Te represents tellurium, component C represents at least one element selected from the group consisting of copper, nickel and cobalt, component D represents at least one element selected from the group consisting of molybdenum, tungsten and vanadium, component F represents at least one element selected from the group consisting of phosphorous and boron, component X represents at least one element selected from the group consisting of tin, titanium, zirconium, niobium, tantalum, chromium, ruthenium, palladium, silver, aluminum, gallium, indium, thallium, germanium, arsenic, bismuth, lanthanum, cerium, praseodymium, neodymium and samarium, component Y represents at least one element selected from the group consisting of magnesium, calcium, strontium, barium, manganese, zinc and lead, component Z represents at least one element selected from the group consisting of lithium, sodium, potassium, rubidium and cesium, O represents oxygen, $SiO_2$ represents silica, a, b, c, d, e, f, x, y, z, g and h represent the atomic ratio of each element (silicon in the case of silica), when a=10, b=5 to 60, c=0.1 to 8.0, d=0.1 to 4.0, e=0.1 to 5.0, f=1.3 to 5.0, x=0 to 5, y=0 to 5, z=0 to 2, h=10 to 200 and g is the atomic ratio of oxygen required to satisfy the valence of each of the elements excluding silicon, and f/d=1 to 5.

In addition, the catalyst for synthesizing acrylonitrile of the present invention preferably contains iron antimonate as a crystal phase.

In addition, the process for producing acrylonitrile of the present invention is characterized by producing acrylonitrile by reacting propylene, molecular oxygen and ammonia in the presence of the catalyst for synthesizing acrylonitrile of the present invention.

Effects of the Invention

According to the catalyst for synthesizing acrylonitrile of the present invention, acrylonitrile can be synthesized at higher yield by inhibiting the formation of by-products.

BEST MODE FOR CARRYING OUT THE INVENTION

The catalyst for synthesizing acrylonitrile of the present invention has a composition represented by the following general formula:

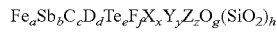

$$Fe_aSb_bC_cD_dTe_eF_fX_xY_yZ_zO_g(SiO_2)_h$$

In the formula, Fe represents iron, Sb represents antimony, Te represents tellurium, component C represents at least one element selected from the group consisting of copper, nickel and cobalt, component D represents at least one element selected from the group consisting of molybdenum, tungsten and vanadium, component F represents at least one element selected from the group consisting of phosphorous and boron, component X represents at least one element selected from the group consisting of tin, titanium, zirconium, niobium, tantalum, chromium, ruthenium, palladium, silver, aluminum, gallium, indium, thallium, germanium, arsenic, bismuth, lanthanum, cerium, praseodymium, neodymium and samarium, component Y represents at least one element selected from the group consisting of magnesium, calcium, strontium, barium, manganese, zinc and lead, component Z represents at least one element selected from the group consisting of lithium, sodium, potassium, rubidium and cesium, O represents oxygen, and $SiO_2$ represents silica.

In addition, in the formula, a, b, c, d, e, f, x, y, z, g and h represent the atomic ratio of each element (silicon in the case of silica), when a=10, b=5 to 60 and preferably 10 to 55, c=0.1 to 8.0 and preferably 0.3 to 7.0, d=0.1 to 4.0 and preferably 0.3 to 3.0, e=0.1 to 5.0 and preferably 0.3 to 4.5, f=1.3 to 5.0 and preferably 1.4 to 4.0, x=0 to 5 and preferably 0 to 4.5, y=0 to 5 and preferably 0 to 4.5, z=0 to 2 and preferably 0 to 1.8, h=10 to 200 and preferably 20 to 180, and g is the atomic ratio of oxygen required to satisfy the valence of each of the elements excluding silicon.

If the atomic ratio of each element contained in the catalyst is outside the aforementioned ranges, the effects of the present invention are not adequately demonstrated due to, for example, the acrylonitrile yield decreasing, thereby making it difficult to achieve the object of the present invention.

Moreover, in the catalyst for synthesizing acrylonitrile of the present invention, the ratio of the atomic ratio d of component D to the atomic ratio f of component F is required to be such that f/d=1 to 5. The lower limit of f/d is preferably 1.1, while the upper limit is preferably 4.8.

In the case the value of f/d is below the lower limit or exceeds the upper limit, the formation of by-products such as hydrocyanic acid increases thereby resulting in a decrease in the yield of acrylonitrile.

Furthermore, in the present invention, the composition of the catalyst for synthesizing acrylonitrile refers to the bulk composition of the catalyst, and provided that remarkably highly volatile components are not used, the catalyst composition (atomic ratio) may be calculated from the charged amounts of the raw materials of each element that composes the catalyst.

In addition, the catalyst for synthesizing acrylonitrile of the present invention preferably contains iron antimonate as a crystal phase. Although there are several types of compositions for iron antimonate (see Patent Document 8), $FeSbO_4$ is the most common, and the presence of a crystal phase thereof can be confirmed by X-ray diffraction analysis. In addition to being in the form of pure iron antimonate, the iron antimonate may also be in the form of a solid solution with various elements.

As a result of containing iron antimonate as the crystal phase, catalyst activity can be improved and physical properties such as particle strength and bulk density can be made to be preferable.

In the case of using the catalyst for synthesizing acrylonitrile of the present invention in a fluidized bed, the shape thereof is preferably spherical. In addition, the outer diameter thereof is preferably within the range of 1 to 200 μm and particularly preferably within the range of 5 to 150 μm.

Although there are no particular limitations on the method for preparing the catalyst for synthesizing acrylonitrile of the present invention, it preferably consists of preparing an aqueous slurry containing raw materials of each element that composes the catalyst, drying the resulting aqueous slurry, and calcining the resulting dried product.

All of elements desired to compose the catalyst may be contained in the aqueous slurry at the desired atomic ratios thereof, and may be added by a method such as impregnation to the catalyst composition after drying or calcining a portion of the elements.

In addition, in the case of preparing a catalyst containing iron antimonate as a crystal phase, a method described in Patent Document 9 or Patent Document 10, for example, can be used.

Namely, an aqueous slurry is prepared containing raw materials of antimony, a trivalent iron component and nitrate ions and the pH of the slurry is adjusted to 7 or lower followed by heat treatment at a temperature within the range of 40 to 150° C., drying the resulting slurry and calcining. This method enables a catalyst to be prepared that contains iron antimonate as a crystal phase.

There are no particular limitations on the raw materials of each element, and oxides of each element, or nitrates, carbonate, organic acid salts, ammonium salts, hydroxides or halides that can easily be converted to oxides by calcining, can be used. In addition, a plurality of types thereof may also be used in combination.

For example, there are no particular limitations on the raw material of the iron component provided it can be easily converted to an oxide. In addition, in the case of preparing a catalyst containing iron antimonate as a crystal phase, the iron is preferably present as a trivalent ion either in solution or in a slurry, preferable examples of which include salts of inorganic acids such as iron (III) nitrate or iron (III) sulfate, salts of organic acids such as iron citrate, and solutions of metallic iron such as electrolytic iron powder dissolved in nitric acid and the like.

There are no particular limitations on the antimony component used, and examples thereof that can be used include oxides such as antimony trioxide or antimony pentoxide, antimony chloride and antimony sulfate.

There are no particular limitations on the tellurium component used, and examples thereof that can be used include tellurium dioxide, telluric acid as well as solutions in which metallic tellurium has been dissolved in nitric acid or aqueous hydrogen peroxide.

There are also no particular limitations on the raw materials of each of the other elements, various types of compounds containing each element can be used in the same manner as described above, and a plurality of types thereof may also be used in combination.

Although there are no particular limitations on the silica raw material, colloidal silica is used preferably. The colloidal silica may be suitably selected from commercially available products.

Although there are no particular limitations on the size of the colloidal particles in the colloidal silica, the mean particle diameter is preferably 2 to 100 nm and more preferably 5 to 75 nm. The size of the colloidal particles of the colloidal silica may be uniform or colloidal particles of several different sizes may be mixed. In addition, a plurality of types of colloidal silica having different mean particle diameter, pH and the like may also be used as a mixture.

There are no particular limitations on the method for drying the aqueous slurry, and a method arbitrarily selected from known methods may be used.

Although the present invention can be applied to either a fixed bed catalyst or fluidized bed catalyst, it is particularly preferably applied to a fluidized bed catalyst.

In the case of producing a fluidized bed catalyst, spherical dry particles are preferably obtained using a spray dryer. A rotating disk-type, nozzle-type or other known type of spray dryer can be used for the spray dryer. During spray drying, spray drying conditions are suitably adjusted so as to obtain a catalyst having physical properties preferable for use as a fluidized bed catalyst, such as particle size distribution and particle strength.

A desirable catalyst structure is formed by calcining the resulting dried product at a temperature within the range of 550 to 1000° C., resulting in the appearance of catalyst activity. Although there are no particular limitations on calcining time, since a satisfactory catalyst is not obtained if the calcining time is too short, the calcining time is preferably 0.5 hours or more and more preferably 1 hour or more. Although there are no particular limitations on the upper limit of calcining time, since effects beyond a certain fixed level thereof are not obtained even if calcining time is extended beyond the required calcining time, the calcining time is normally 20 hours or less. There are no particular limitations on the calcining method, and a method using a general-purpose calcining furnace can be used. In the case of producing a fluidized bed catalyst, a rotary kiln or fluidized bed calciner and the like is used particularly preferably.

During calcining, although the dried product may be immediately calcined at a temperature within the range of 550 to 1000° C., there are cases in which catalyst physical properties and activity are improved by carrying out calcining by preliminarily calcining in one to two stages at a temperature within the range of 250 to 500° C. followed by calcining at a temperature within the range of 550 to 1000° C.

When synthesizing acrylonitrile by vapor phase ammoxidation of propylene by molecular oxygen (to simply be referred to as oxygen) and ammonia using the catalyst for synthesizing acrylonitrile of the present invention, it is preferable to use a fluidized bed reactor.

The concentration of propylene in the raw material gas when carrying out vapor phase ammoxidation can be varied over a wide range, is suitably 1 to 20% by volume and particularly preferably 3 to 15% by volume.

The molar ratio of propylene to oxygen in the raw material gas (propylene:oxygen) is preferably 1:1.5 to 1:3. Although air is industrially advantageously used for the oxygen source, oxygen-enriched air may also be used as necessary by adding pure oxygen.

In addition, the molar ratio of propylene to ammonia in the reaction gas (propylene:ammonia) is preferably 1:1 to 1:1.5.

The raw material gas may be diluted with an inert gas or water vapor and the like.

The vapor phase ammoxidation reaction is normally carried out at a reaction temperature of 370 to 500° C. and a reaction pressure is atmospheric pressure to 500 kPa, the apparent contact time between the catalyst and raw material gas is 1 to 20 seconds.

Furthermore, in the present invention, "apparent contact time" refers to the value determined according to the formula indicated below.

Apparent contact time (sec)=volume of catalyst based on apparent bulk density (mL)/amount of raw material gas converted to the reaction conditions (mL/sec)

EXAMPLES

Although effects of the present invention are indicated using the following examples and comparative examples, the present invention is not limited whatsoever by the following examples.

Example 1

A catalyst having the composition shown in Table 1 was prepared according to the procedure described below.

First, 63.5 g of copper powder were dissolved in 2400 g of 63% by weight nitric acid. 2300 g of pure water were added to this solution followed by heating to 60° C., gradually adding 185.9 g of electrolytic iron powder and 42.5 g of tellurium powder and dissolving. After confirming dissolution, 96.8 g of nickel nitrate, 40.0 g of chromium nitrate, 9.6 g of manganese nitrate and 1.2 g of lithium nitrate were sequentially added and dissolved (Liquid A).

Separate from the above procedure, a solution in which 34.8 g of ammonium paratungstate were dissolved in 800 g of pure water (Liquid B), and a solution in which 29.4 g of ammonium paramolybdate were dissolved in 100 g of pure water (Liquid C), were respectively prepared.

Next, 5998.4 g of 20% by weight colloidal silica, 1212.7 g of antimony trioxide powder, Liquid B and Liquid C were sequentially added to Liquid A while stirring to obtain an aqueous slurry.

15% by weight aqueous ammonia was dropped into this aqueous slurry to adjust the pH to 2.0 followed by heat-treating the resulting aqueous slurry for 3 hours at the boiling point while refluxing.

Following completion of heat treatment, the aqueous slurry was cooled to 80° C. followed by the addition of 19.2 g of 85% by weight phosphoric acid and 37.0 g of boric acid.

The resulting aqueous slurry was spray-dried with a spray dryer at a temperature of the drying air at the dryer inlet of 330° C. and a temperature at the dryer outlet of 160° C. to obtain spherical dry particles. Next, the resulting dry particles were calcined for 2 hours at 250° C. and then for 2 hours at 400° C. followed finally by carrying out fluidized calcining for 3 hours at 800° C. using a fluidized bed calciner to obtain a catalyst for synthesizing acrylonitrile.

<Activity Testing>

An acrylonitrile synthesis reaction was carried out by vapor phase contact ammoxidation of propylene according to the procedure described below using the resulting catalyst.

The catalyst was filled into a fluidized bed reactor having an inner diameter of 55 mm and height of 2000 mm for the catalyst flow portion so that the apparent contact time between the catalyst and the raw material gas was as shown in Table 2. The contact time at that time was determined according to the formula indicated below.

Apparent contact time (sec)=volume of catalyst based on apparent bulk density (mL)/amount of raw material gas converted to the reaction conditions (mL/sec)

Air was used for the oxygen source, and a raw material gas composed of propylene, ammonia and oxygen at a molar ratio of 1:1.1:2.3 was fed to the catalyst layer at a gas linear velocity of 17 cm/sec. The reaction pressure was set to 200 kPa and the reaction temperature was set to 460° C.

Chromatography was used to quantify the reaction product, and the propylene conversion rate and acrylonitrile yield were determined 4 hours after the start of the reaction. The propylene conversion rate and acrylonitrile yield at that time were determined according to the formula indicated below. The results are shown in Table 2.

Propylene conversion rate (%)=(number of moles of propylene consumed in the reaction/number of moles of propylene supplied as raw material gas)×100

Acrylonitrile yield (%)=(number of moles of acrylonitrile formed/number of moles of propylene supplied as raw material gas)×100

Example 2

A catalyst having the composition shown in Table 1 was prepared according to the procedure described below.

First, 58.4 g of copper powder were dissolved in 1800 g of 63% by weight nitric acid. 1700 g of pure water were added to this solution followed by heating to 60° C., gradually adding 128.2 g of electrolytic iron powder and 64.5 g of tellurium powder and dissolving. After confirming dissolution, 133.6 g of cobalt nitrate, 30.7 g of zirconium oxynitrate, 17.2 g of aluminum nitrate and 34.2 g of zinc nitrate were sequentially added and dissolved (Liquid D).

Separate from the above procedure, a solution in which 16.1 g of ammonium metavanadate were dissolved in 400 g of pure water (Liquid E), and a solution in which 60.8 g of ammonium paramolybdate were dissolved in 200 g of pure water (Liquid F), were respectively prepared.

Next, 5517.9 g of 20% by weight colloidal silica, 1338.7 g of antimony trioxide powder, Liquid E and Liquid F were sequentially added to Liquid D while stirring to obtain an aqueous slurry.

15% by weight aqueous ammonia was dropped into this aqueous slurry to adjust the pH to 2.2 followed by heat-treating the resulting aqueous slurry for 3 hours at the boiling point while refluxing.

Following completion of heat treatment, the aqueous slurry was cooled to 80° C. followed by the addition of 5.3 g of 85% by weight phosphoric acid and 34.1 g of boric acid.

The resulting aqueous slurry was spray-dried with a spray dryer at a temperature of the drying air at the dryer inlet of 330° C. and a temperature at the dryer outlet of 160° C. to obtain spherical dry particles. Next, the resulting dry particles were calcined for 2 hours at 250° C. and then for 2 hours at 400° C. followed finally by carrying out fluidized calcining for 3 hours at 820° C. using a fluidized bed calciner to obtain a catalyst for synthesizing acrylonitrile.

Activity testing was carried out on the resulting catalyst in the same manner as Example 1. The results are shown in Table 2.

Example 3

A catalyst having the composition shown in Table 1 was prepared according to the procedure described below.

First, 1500 g of pure water were added to 1700 g of 63% by weight nitric acid followed by heating to 60° C., gradually adding 136.4 g of electrolytic iron powder and 37.4 g of tellurium powder and dissolving. After confirming dissolution, 198.8 g of nickel nitrate, 92.4 g of cobalt nitrate, 10.6 g of lanthanum nitrate, 14.0 g of manganese nitrate and 2.5 g of potassium nitrate were sequentially added and dissolved (Liquid G).

Separate from the above procedure, a solution in which 38.3 g of ammonium paratungstate were dissolved in 950 g of pure water (Liquid H), and a solution in which 34.5 g of ammonium paramolybdate were dissolved in 100 g of pure water (Liquid I), were respectively prepared.

Next, 7335.8 g of 20% by weight colloidal silica, 1067.9 g of antimony trioxide powder, Liquid H and Liquid I were sequentially added to Liquid G while stirring to obtain an aqueous slurry.

15% by weight aqueous ammonia was dropped into this aqueous slurry to adjust the pH to 2.0 followed by heat-treating the resulting aqueous slurry for 3 hours at the boiling point while refluxing.

Following completion of heat treatment, the aqueous slurry was cooled to 80° C. followed by the addition of 30.2 g of boric acid.

The resulting aqueous slurry was spray-dried with a spray dryer at a temperature of the drying air at the dryer inlet of 330° C. and a temperature at the dryer outlet of 160° C. to obtain spherical dry particles. Next, the resulting dry particles were calcined for 2 hours at 250° C. and then for 2 hours at 400° C. followed finally by carrying out fluidized calcining for 3 hours at 780° C. using a fluidized bed calciner to obtain a catalyst for synthesizing acrylonitrile.

Activity testing was carried out on the resulting catalyst in the same manner as Example 1. The results are shown in Table 2.

Example 4

A catalyst having the composition shown in Table 1 was prepared according to the procedure described below.

First, 25.2 g of copper powder were dissolved in 3100 g of 63% by weight nitric acid. 2800 g of pure water were added to this solution followed by heating to 60° C., gradually adding 277.2 g of electrolytic iron powder and 50.7 g of tellurium powder and dissolving. After confirming dissolution, 86.6 g of nickel nitrate, 38.2 g of magnesium nitrate, 28.5 g of manganese nitrate and 5.9 g of rubidium nitrate were sequentially added and dissolved (Liquid J).

Separate from the above procedure, a solution in which 38.9 g of ammonium paratungstate were dissolved in 900 g of pure water (Liquid K), a solution in which 35.1 g of ammonium paramolybdate were dissolved in 100 g of pure water (Liquid L), and a solution in which 5.8 g of ammonium metavanadate were dissolved in 150 g of pure water (Liquid M) were respectively prepared.

Next, 5962.9 g of 20% by weight colloidal silica, 1085.0 g of antimony trioxide powder, Liquid K, Liquid L and Liquid M were sequentially added to Liquid J while stirring to obtain an aqueous slurry.

15% by weight aqueous ammonia was dropped into this aqueous slurry to adjust the pH to 2.2 followed by heat-treating the resulting aqueous slurry for 3 hours at the boiling point while refluxing.

Following completion of heat treatment, the aqueous slurry was cooled to 80° C. followed by the addition of 34.3 g of 85% by weight phosphoric acid and 76.7 g of boric acid.

The resulting aqueous slurry was spray-dried with a spray dryer at a temperature of the drying air at the dryer inlet of 330° C. and a temperature at the dryer outlet of 160° C. to obtain spherical dry particles. Next, the resulting dry particles were calcined for 2 hours at 250° C. and then for 2 hours at 400° C. followed finally by carrying out fluidized calcining for 3 hours at 750° C. using a fluidized bed calciner to obtain a catalyst for synthesizing acrylonitrile.

Activity testing was carried out on the resulting catalyst in the same manner as Example 1. The results are shown in Table 2.

Example 5

A catalyst having the composition shown in Table 1 was prepared according to the procedure described below.

First, 59.6 g of copper powder were dissolved in 2400 g of 63% by weight nitric acid. 2200 g of pure water were added to this solution followed by heating to 60° C., gradually adding 200.0 g of electrolytic iron powder and 36.6 g of tellurium powder and dissolving (Liquid N).

Separate from the above procedure, a solution in which 25.3 g of ammonium paramolybdate were dissolved in 100 g of pure water (Liquid O), a solution in which 46.8 g of ammonium paratungstate were dissolved in 1200 g of pure water (Liquid P), and a solution in which 41.1 g of telluric acid were dissolved in 300 g of pure water (Liquid Q) were respectively prepared.

Next, 5379.1 g of 20% by weight colloidal silica, 1305.0 g of antimony trioxide powder, Liquid O and Liquid P were sequentially added to Liquid N while stirring to obtain an aqueous slurry.

15% by weight aqueous ammonia was dropped into this aqueous slurry to adjust the pH to 2.2 followed by heat-treating the resulting aqueous slurry for 3 hours at the boiling point while refluxing.

Following completion of heat treatment, the aqueous slurry was cooled to 80° C. followed by the sequential addition of 83.3 g of nickel nitrate, 8.3 g of 85% by weight phosphoric acid, 48.7 g of boric acid and Liquid Q.

The resulting aqueous slurry was spray-dried with a spray dryer at a temperature of the drying air at the dryer inlet of 330° C. and a temperature at the dryer outlet of 160° C. to obtain spherical dry particles. Next, the resulting dry particles were calcined for 2 hours at 250° C. and then for 2 hours at 400° C. followed finally by carrying out fluidized calcining for 3 hours at 800° C. using a fluidized bed calciner to obtain a catalyst for synthesizing acrylonitrile.

Activity testing was carried out on the resulting catalyst in the same manner as Example 1. The results are shown in Table 2.

Example 6

A catalyst having the composition shown in Table 1 was prepared according to the procedure described below.

First, 72.6 g of copper powder were dissolved in 2400 g of 63% by weight nitric acid. 2200 g of pure water were added to this solution followed by heating to 60° C., gradually adding 182.3 g of electrolytic iron powder and 41.6 g of tellurium powder and dissolving. After confirming dissolution, 47.5 g of nickel nitrate, 47.5 g of cobalt nitrate and 15.8 g of bismuth nitrate were sequentially added and dissolved (Liquid R).

Separate from the above procedure, 28.8 g of ammonium paramolybdate and 25.0 g of tellurium powder were suspended in 200 g of pure water and heated to 80° C. followed by dropping in 80 g of 35% by weight aqueous hydrogen peroxide and dissolving (Liquid S).

Next, 5881.7 g of 20% by weight colloidal silica and 1189.1 g of antimony trioxide powder were sequentially added to Liquid R while stirring to obtain an aqueous slurry.

15% by weight aqueous ammonia was dropped into this aqueous slurry to adjust the pH to 2.1 followed by heat-treating the resulting aqueous slurry for 3 hours at the boiling point while refluxing.

Following completion of heat treatment, the aqueous slurry was cooled to 80° C. followed by the sequential addition of 18.8 g of 85% by weight phosphoric acid, 24.2 g of boric acid, 105.9 g of 50% by weight aqueous ammonium metatungstate solution and Liquid S.

The resulting aqueous slurry was spray-dried with a spray dryer at a temperature of the drying air at the dryer inlet of 330° C. and a temperature at the dryer outlet of 160° C. to obtain spherical dry particles. Next, the resulting dry particles were calcined for 2 hours at 250° C. and then for 2 hours at 400° C. followed finally by carrying out fluidized calcining for 3 hours at 790° C. using a fluidized bed calciner to obtain a catalyst for synthesizing acrylonitrile.

Activity testing was carried out on the resulting catalyst in the same manner as Example 1. The results are shown in Table 2.

Comparative Example 1

A catalyst having the composition shown in Table 1 was prepared using the same procedure as Example 1 with the exception of not adding boric acid.

Activity testing was carried out on the resulting catalyst in the same manner as Example 1. The results are shown in Table 2.

Comparative Example 2

A catalyst having the composition shown in Table 1 was prepared using the same procedure as Example 1 with the exception of adjusting the amount of raw material of each element added.

Activity testing was carried out on the resulting catalyst in the same manner as Example 1. The results are shown in Table 2.

Comparative Example 3

A catalyst having the composition shown in Table 1 was prepared using the same procedure as Example 3 with the exception of not adding boric acid.

Activity testing was carried out on the resulting catalyst in the same manner as Example 1. The results are shown in Table 2.

Comparative Examples 4 and 5

Catalysts having the composition shown in Table 1 were prepared using the same procedure as Example 5 with the exception of adjusting the amount of raw material of each element added.

Activity testing was carried out on the resulting catalysts in the same manner as Example 1. The results are shown in Table 2.

Comparative Example 6

A catalyst having the composition shown in Table 1 was prepared using the same procedure as Example 6 with the exception of not adding tellurium powder.

Activity testing was carried out on the resulting catalyst in the same manner as Example 1. The results are shown in Table 2.

TABLE 1

| | | Fe | Sb | C | | | D | | | Te | F | | X | | Y | | Z | Si | f/d |
|---|---|---|---|---|---|---|---|---|---|---|---|---|---|---|---|---|---|---|---|
| Examples | 1 | 10 | 25 | Cu 3.0 | Ni 1.0 | | Mo 0.5 | W 0.4 | | 1.0 | P 0.5 | B 1.8 | Cr 0.3 | | Mn 0.1 | | Li 0.05 | 60 | 2.56 |
| | 2 | 10 | 40 | Cu 4.0 | Co 2.0 | | Mo 1.5 | V 0.6 | | 2.2 | P 0.2 | B 2.4 | Zr 0.5 | Al 0.2 | Zn 0.5 | | | 80 | 1.24 |
| | 3 | 10 | 30 | Ni 2.8 | Co 1.3 | | Mo 0.8 | W 0.6 | | 1.2 | | B 2.0 | La 0.1 | | Mn 0.2 | | K 0.1 | 100 | 1.43 |
| | 4 | 10 | 15 | Cu 0.8 | Ni 0.6 | | Mo 0.4 | W 0.3 | V 0.1 | 0.8 | P 0.6 | B 2.5 | | | Mg 0.3 | Mn 0.2 | Rb 0.08 | 40 | 3.88 |
| | 5 | 10 | 25 | Cu 2.5 | Ni 0.8 | | Mo 0.4 | W 0.5 | | 1.3 | P 0.2 | B 2.2 | | | | | | 50 | 2.67 |
| | 6 | 10 | 25 | Cu 3.5 | Ni 0.5 | Co 0.5 | Mo 0.5 | W 0.7 | | 1.6 | P 0.5 | B 1.2 | Bi 0.1 | | | | | 60 | 1.42 |
| Comparative Examples | 1 | 10 | 25 | Cu 3.0 | Ni 1.0 | | Mo 0.5 | W 0.4 | | 1.0 | P 0.5 | | Cr 0.3 | | Mn 0.1 | | Li 0.05 | 60 | 0.56 |
| | 2 | 10 | 25 | Cu 3.0 | Ni 1.0 | | Mo 2.6 | W 0.4 | | 1.0 | P 0.5 | B 1.8 | Cr 0.3 | | Mn 0.1 | | Li 0.05 | 60 | 0.77 |
| | 3 | 10 | 30 | Ni 2.8 | Co 1.3 | | Mo 0.8 | W 0.6 | | 1.2 | | | La 0.1 | | Mn 0.2 | | K 0.1 | 100 | 0.00 |
| | 4 | 10 | 25 | Cu 2.5 | Ni 0.8 | | Mo 0.1 | W 0.2 | | 1.3 | P 0.2 | B 2.2 | | | | | | 50 | 8.00 |
| | 5 | 10 | 25 | Cu 2.5 | Ni 0.8 | | Mo 0.2 | W 0.3 | | 1.3 | P 0.4 | B 4.4 | | | | | | 50 | 9.60 |
| | 6 | 10 | 25 | Cu 3.5 | Ni 0.5 | Co 0.5 | Mo 0.5 | W 0.7 | | | P 0.5 | B 1.2 | Bi 0.1 | | | | | 60 | 1.42 |

TABLE 2

| | | Calcining Temp. (°C.) | Apparent contact time (sec) | Propylene conversion rate (%) | Acrylonitrile yield (%) |
|---|---|---|---|---|---|
| Examples | 1 | 800 | 2.5 | 98.4 | 82.1 |
| | 2 | 820 | 3.2 | 98.2 | 81.6 |
| | 3 | 780 | 3.5 | 98.8 | 81.2 |
| | 4 | 750 | 2.8 | 98.0 | 80.9 |
| | 5 | 800 | 2.6 | 98.4 | 82.1 |
| | 6 | 790 | 2.5 | 98.8 | 82.0 |
| Comparative Examples | 1 | 800 | 2.5 | 98.6 | 81.0 |
| | 2 | 800 | 2.5 | 99.2 | 80.4 |
| | 3 | 780 | 3.5 | 98.9 | 79.6 |
| | 4 | 800 | 2.6 | 97.9 | 80.8 |
| | 5 | 800 | 2.6 | 96.8 | 79.3 |
| | 6 | 790 | 2.5 | 99.4 | 77.6 |

As is clear from Table 2, in the case of using the catalysts for synthesizing acrylonitrile obtained in the examples, acrylonitrile was able to be synthesized at a high yield of 80% or more in all cases.

On the other hand, in the case of using the catalysts for synthesizing acrylonitrile obtained in the comparative examples, the yields of acrylonitrile were lower in comparison with the examples.

INDUSTRIAL APPLICABILITY

According to the catalyst for synthesizing acrylonitrile of the present invention, a high yield of acrylonitrile can be achieved when synthesizing acrylonitrile by vapor phase ammoxidation of propylene.

Namely, the use of the catalyst for synthesizing acrylonitrile of the present invention enables acrylonitrile to be produced industrially advantageously, thereby allowing the catalyst for producing acrylonitrile of the present invention to have considerable industrial value.

The invention claimed is:

1. A catalyst for synthesizing acrylonitrile having the composition represented by the following general formula:

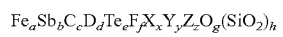

$Fe_aSb_bC_cD_dTe_eF_fX_xY_yZ_zO_g(SiO_2)_h$ (wherein, Fe represents iron, Sb represents antimony, Te represents tellurium, component C represents at least one element selected from the group consisting of copper, nickel and cobalt, component D represents at least one element selected from the group consisting of molybdenum, tungsten and vanadium, component F represents at least one element selected from the group consisting of phosphorous and boron, component X represents at least one element selected from the group consisting of tin, titanium, zirconium, niobium, tantalum, chromium, ruthenium, palladium, silver, aluminum, gallium, indium, thallium, germanium, arsenic, bismuth, lanthanum, cerium, praseodymium, neodymium and samarium, component Y represents at least one element selected from the group consisting of magnesium, calcium, strontium, barium, manganese, zinc and lead, component Z represents at least one element selected from the group consisting of lithium, sodium, potassium, rubidium and cesium, O represents oxygen, $SiO_2$ represents silica, a, b, c, d, e, f, x, y, z, g and h represent the atomic ratio of each element (silicon in the case of silica), when a=10, b=5 to 60, c=0.1 to 8.0, d=0.1 to 4.0, e=0.1 to 5.0, f=1.3 to 5.0, x=0 to 5, y=0 to 5, z=0 to 2, h=10 to 200 and g is the atomic ratio of oxygen required to satisfy the valence of each of the elements excluding silicon, and f/d=1 to 5).

2. The catalyst for synthesizing acrylonitrile according to claim 1, wherein iron antimonate is contained as a crystal phase.

3. A process for producing acrylonitrile, comprising: producing acrylonitrile by reacting propylene, molecular oxygen and ammonia in the presence of the catalyst for synthesizing acrylonitrile according to claim 1 or 2.

* * * * *